United States Patent
Wada et al.

(10) Patent No.: US 10,702,354 B2
(45) Date of Patent: Jul. 7, 2020

(54) RF TAG MARKER, EMISSION MARKER, AND THE DETECTOR

(71) Applicant: Osaka Prefectural Hospital Organization, Osaka-shi, Osaka (JP)

(72) Inventors: Yuma Wada, Osaka (JP); Norikatsu Miyoshi, Osaka (JP); Masayuki Ohue, Osaka (JP); Masayoshi Yasui, Osaka (JP); Masato Sakon, Osaka (JP)

(73) Assignee: Osaka Prefectural Hospital Organization, Osaka (JP)

(*) Notice: Subject to any disclaimer, the term of this patent is extended or adjusted under 35 U.S.C. 154(b) by 463 days.

(21) Appl. No.: 15/290,962

(22) Filed: Oct. 11, 2016

(65) Prior Publication Data
US 2017/0105810 A1 Apr. 20, 2017

(30) Foreign Application Priority Data

Oct. 15, 2015 (JP) ................................. 2015-204030
Jul. 14, 2016 (JP) ................................. 2016-139776

(51) Int. Cl.
*A61B 5/00* (2006.01)
*A61B 90/00* (2016.01)
*A61B 90/98* (2016.01)

(52) U.S. Cl.
CPC .............. *A61B 90/39* (2016.02); *A61B 90/98* (2016.02); *A61B 2090/3908* (2016.02); *A61B 2090/3945* (2016.02); *A61B 2090/3975* (2016.02); *A61B 2090/3987* (2016.02); *A61B 2090/3991* (2016.02)

(58) Field of Classification Search
CPC . A61B 90/39; A61B 90/98; A61B 2090/3987; A61B 2090/3991; A61B 2090/3975; A61B 2090/3945; A61B 2090/3908
See application file for complete search history.

(56) References Cited

U.S. PATENT DOCUMENTS

2005/0182318 A1   8/2005  Kaji et al.
2008/0064006 A1*  3/2008  Quan ................... A61C 1/0015
                                                    433/119

FOREIGN PATENT DOCUMENTS

JP    2002-113018 A    4/2002
JP    2005-204694 A    8/2005
JP    2005-218680 A    8/2005
(Continued)

OTHER PUBLICATIONS

Cho et al., "Tumor Localization for Laparoscopic Colorectal Surgery," World J Surg, vol. 31, 2007, pp. 1491-1495.
(Continued)

*Primary Examiner* — Joel Lamprecht
(74) *Attorney, Agent, or Firm* — Foley & Lardner LLP

(57) ABSTRACT

An object of the present invention is to provide an emission marker for being indwelled in a lumen, the emission marker having: a base part; a coil wound around the base part; an emission part electrically connected to the coil; and a cover part for covering at least the base part and the coil, wherein the emission part has a light source that emits visible light. Additionally, the present invention relates to a detector for detecting, from outside of a lumen, an emission marker indwelled in the lumen, the detector having a detection unit having an antenna that acts with a coil of the emission marker.

9 Claims, 11 Drawing Sheets

(56) References Cited

FOREIGN PATENT DOCUMENTS

JP  2006-271832 A  10/2006
JP  2010-000284 A   1/2010

OTHER PUBLICATIONS

Luigiano et al., "Endoscopic Tattooing of Gastrointestinal and Pancreatic Lesions," Adv Ther, vol. 29, No. 10, 2012, pp. 864-873.
Notice of Reasons for Refusal issued in Japan Application No. 2016-139776 dated Nov. 28, 2019, 12 pages.

* cited by examiner (a)

(b)

(c)

(d)

RF TAG MARKER, EMISSION MARKER, AND THE DETECTOR

CROSS-REFERENCE TO RELATED PATENT APPLICATIONS

This application claims priority to Japanese Application No. 2015-204030, filed Oct. 15, 2015, and Japanese Application No. 2016-139776, filed Jul. 14, 2016, the content of each of which is incorporated herein by reference in its entirety.

BACKGROUND OF THE INVENTION

Field of the Invention

The present invention relates to an RF tag marker and an emission marker used for marking a tumor inside a lumen, and a detector for detecting the same.

Description of the Related Art

In a surgical operation, it is very important to accurately determine a lesion site to determine an excisional range (Cho, Y. B., et al.: Tumor localization for laparoscopic colorectal surgery. World J Surg, 31 (7): 1491-5, 2007.). Therefore, in a test before surgery, the lesion site is marked in order to identify the excisional range. Generally, a dye method is used in the test before surgery (Luigiano, C., et al.: Endoscopic tattooing of gastrointestinal and pancreatic lesions. Adv Ther, 29 (10) 864-73, 2012.).

In a tattooing method which is a representative example of the dye method, India ink is injected inside the mucosa of a stomach or a large intestine, or in a submucosal layer, so that black spots are attached in the vicinity of the lesion site, as a sign.

In a recent surgical operation, in place of laparotomy, laparoscopic surgery in which a site to be incised is minimized is often used. The use of laparoscopic surgery results in various advantages such as that early recovery after surgery is expected, and postoperative adhesion complications can be suppressed. In a case where laparoscopic surgery or laparotomy is performed, a tumor cannot be visually recognized from the serosal surface of an intestinal tract, and therefore intraoperative endoscopy is used at the same time, in order to particularly identify an accurate excisional range. The intraoperative endoscopy is used at the same time, so that the position of a tumor is confirmed from the inside of a lumen, and an excisional range is easily identified.

However, in the tattooing method conventionally used, an accurate excisional range cannot sometimes be identified by diffusion of India ink from an injected site, or peritonitis is sometimes caused by leakage of India ink into an abdominal cavity. Additionally, as described above, in the case where the intraoperative endoscopy is used at the same time, a human burden, an economic burden, extension of a surgery time, and the like greatly influence a patient.

Particularly, in a digestive organ cancer region, an operative method is determined by a lesion site, and therefore selection of the operative method is sometimes difficult in marking by use of only dye, and there is concern over having a large influence on increase in operative stress to a patient, and decrease in postoperative QOL due to an unnecessarily wide range of excision.

The present invention has been made in view of the above circumstances, and an object of the present invention is to provide an RF tag marker and an emission marker that can be easily and safely used, and are capable of identifying an accurate lesion site and an accurate excisional range, and a detector for the same.

SUMMARY OF THE INVENTION

That is, the present invention relates to an RF tag marker for being indwelled in a lumen, the RF tag marker comprising:

a body; and a perforation part provided in the body.

In an embodiment of the above invention, the RF tag marker has an antenna, a memory, and a control circuit. The memory and the control circuit can be configured by an IC chip. A detector (e.g., reader/writer) described below can read/write information of the memory.

In an embodiment of the above invention, the memory can record identification information.

In an embodiment of the above invention, the perforation part may be provided at a site where the body is perforated. The perforation part may be continuously provided to be adjacent to the body. The perforation part may be connected to at least one end of the body and be provided so as to wrap around the body with a predetermined gap therebetween. The number of the perforation parts may be one, or may be a plural number. In a case where the perforation part is provided at the site where the body is perforated, the perforation part can be provided at a central part of the body or at an outside position deviated from the central part. The perforation part is preferably provided at the outside position deviated from the central part of the body, in order that while the RF tag marker is inserted into a clip for an endoscope or the like, and an opening/closing arm is closed, the RF tag marker can be inserted into a forceps channel or the like. The gap can be provided in a range so as to enable insertion into the clip for an endoscope.

In an embodiment of the above invention, an opening/closing arm of a clip for an endoscope has at least one claw part of the clip for an endoscope. The perforation part is inserted around at least one of the claw parts. The clip for an endoscope may have a plurality of the claw parts, and the number of the claw parts may be two or three. Additionally, the clip for an endoscope may have further more number of the claw part. In an embodiment of the above invention, the perforation part can be inserted around at least one of the claw parts of the clip for an endoscope.

A tip on a distal side of the claw part may have a protrusion protruding inward (sandwiching direction) of the clip for an endoscope. The protrusion is provided, so that a tissue such as mucosa is easily grasped, and the clip for an endoscope is easily indwelled in an intestinal tract wall of a lumen.

In this specification, the term "distal" means a distal side from a side where an operator of an endoscope or the like operates. Additionally, the term "proximal" means a proximal side from a side where the operator of the endoscope or the like operates.

In this specification, the term "inward" of the clip for an endoscope means the direction toward the central axis of the clip for an endoscope or an extension line of this central axis, and includes the inward direction in the radial direction.

In a case where the perforation part is inserted around the claw part of the clip for an endoscope, a contact surface of the perforation part with the claw part of the opening/closing arm of the clip for an endoscope is preferably equal or slightly smaller, from a viewpoint of preventing the RF tag marker from being easily detached from the clip for an endoscope due to operation during surgery. With such a configuration, the RF tag marker can be inserted around a claw part of every clip for an endoscope. The insertion of the RF tag marker around the claw part of the clip for an endoscope can be also performed by an operator before surgery. Additionally, the clip for an endoscope with the RF tag marker being previously inserted around the claw part can be sold.

In an embodiment of the above invention, when the perforation part is inserted around at least the one claw part of the opening/closing arm of the clip for an endoscope, the body is disposed inward of the opening/closing arm of the clip for an endoscope. Consequently, in a state where the opening/closing arm of the clip for an endoscope is closed, the RF tag marker is located more on the inner side than the maximum diameter of the closed opening/closing arm of the clip for an endoscope, and can be inserted into a forceps channel of an endoscope or the like.

In an embodiment of the above invention, the perforation part can be formed of a biocompatible material. In a case where the perforation part is provided at the site where the body is perforated, an entire outer wall including the perforation part in the RF tag marker can be formed of the biocompatible material. In a case where the perforation part is continuously provided to be adjacent to the body, or is connected to at least the one end of the body and is provided so as to wrap around the body with the predetermined gap therebetween, the perforation part can be formed of a film material, and this film material can be formed of the biocompatible material. The site where the entire periphery of the RF tag marker is covered may be formed of the biocompatible material. The biocompatible material is at least one kind selected from the group consisting of silicone, polyethylene, polyester, nylon, cellophane, and acetate.

In an embodiment of the above invention, the RF tag marker has a size enabling insertion into a forceps channel of an endoscope (forceps hole in this specification). Additionally, in a state where the RF tag marker is set in the clip for an endoscope, the RF tag marker and the clip for an endoscope may have a size enabling insertion into the forceps channel of the endoscope. The size of the RF tag marker is reduced up to such a degree as to be inserted into the forceps channel of the endoscope, so that clinical usefulness is enhanced, and the RF tag marker is formed in such a shape as to be easily indwelled under the endoscope.

In an embodiment of the above invention, the inner diameter of the forceps channel is 2 mm to 10 mm. In a case where a digestive tract endoscope is used, the inner diameter of the forceps channel is preferably 5 mm or less, and is more preferably 3 mm or less. Accordingly, the size of the RF tag marker is preferably smaller than the inner diameter of the forceps channel. The maximum diameter of a surface orthogonal to the longitudinal direction of the RF tag marker is preferably 10 mm or less, is more preferably 5 mm or less, is particularly preferably 3 mm or less, and is most preferably 2 mm or less. Although not limited, the body of the RF tag marker can be formed in a rectangular parallelepiped shape.

In an embodiment of the above invention, the RF tag marker is indwelled in the tumor vicinity along with the clip for an endoscope. In this specification, the term "vicinity" of the tumor means that a tumor is near enough to enable identification of the position of the tumor. When the indwelled position is too far from the tumor, identification of a lesion site is unclear, and when the indwelled position is right above the tumor, a tumor tissue may be damaged, which is not preferable. The indwelled position is not limited as long as the identification of the lesion site is clear. For example, the indwelled position is preferably 3 cm or less from a tumor, is more preferably 2 cm or less, and is further more preferably 1 cm or less.

The present invention can be a clip for an endoscope in which the RF tag marker is set. For example, the claw part of the clip for an endoscope is disposed in the perforation part of the RF tag marker, so that the RF tag marker is set in the clip for an endoscope.

The present invention can be a kit including the RF tag marker, and the clip for an endoscope.

The present invention relates to a detector for detecting, from outside of a lumen, an RF tag marker indwelled in the lumen, the detector having a detection unit having: an antenna capable of communicating with the RF tag marker; and a reader.

In an embodiment of the above invention, the detection unit may further have a support part provided in the detection unit. The support part can be rigid or flexible. Although not limited, in a case where the support part is rigid, the support part can be a bar-shape. In a case where the support part is flexible, the support part can be freely bent, and the bent state can be preferably held.

In an embodiment of the above invention, the RF tag marker is an electromagnetic induction system passive tag, or an electric wave system passive tag.

In an embodiment of the above invention, the reader can read information of an IC chip provided in the RF tag marker.

In an embodiment of the above invention, the detection unit further has a writer. The writer can write data in the IC chip.

In an embodiment of the above invention, the detector further has a power supply.

In an embodiment of the above invention, the detector further has a monitor.

In an embodiment of the above invention, the detection unit has a notification unit which outputs that the reader has read information of the IC chip.

In an embodiment of the above invention, the notification unit notifies detection by sound or monitor display.

In an embodiment of the above invention, the detection unit communicates with the RF tag marker by an electromagnetic induction system or an electric wave system.

In an embodiment of the above invention, at least the detection unit and the support part can be inserted into a laparoscope port (also referred to as a trocar in this specification).

In an embodiment of the above invention, the inner diameter of the laparoscope port is 2 mm to 20 mm.

In an embodiment of the above invention, at least the detection unit and the support part are formed to be high-temperature and high-pressure steam sterilizable.

In an embodiment of the above invention, at least one part of each of the detection unit and the support part is made of oxygen free copper, silicone, polycarbonate, polypropylene, polyolefin, polysulfone, polyethylene terephthalate, polybutylene terephthalate, Teflon (registered trademark), rubber-like polymer, or polyvinyl chloride. Although not limited, a base plate where the antenna and the reader are disposed in the detection unit is covered by a high-temperature and high-pressure steam sterilizable material such as those above, so that the body of the detector can be formed. Although not limited, in the support part, the covering material of a wire can be formed of a high-temperature and high-pressure steam sterilizable material such as those above. From a viewpoint of prominently exerting an effect of the present invention, at least one part of each of the detection unit and the support part are preferably made of oxygen free copper or silicone. In a case where constant flexibility is given to the support part of the detector, an insulating film having flexibility such as films made of silicone and polyvinyl chloride is preferably used.

Additionally, the present invention relates to an emission marker for being indwelled in a lumen comprising:
- a base part;
- a coil wound around the base part;
- an emission part electrically connected to the coil; and
- a cover part for covering at least the base part and the coil, wherein
the emission part has a light source that emits visible light.

In this specification, the term "emission marker" means a device that enables identification of an indwelled position by visible light. A magnetic flux or a radio wave from a detector described below acts, so that a current is generated by electromagnetic induction or resonance to be supplied to the emission part, and the emission marker emits visible light.

The emission marker may have a control circuit. The control circuit is connected between the coil and the emission part, so that the control circuit can control a current to be supplied from the coil to the emission part. Although not limited, a current is set so as not to be supplied to the emission part at a constant current value or less, so that it is possible to adjust a detectable distance of the emission marker. The emission part may be provided at one end of the base part.

Although not limited, the wavelength of the visible light can be 380 nm to 780 nm. The emission marker is indwelled in a lumen having a lesion site such as a tumor, and is detected from the outside of the lumen by a detector described below. Therefore, the color of visible light is preferably a color which easily penetrates a wall surface of an organ. For example, the color can be red or orange. Additionally, from a viewpoint of permeability of the wall surface of the organ, the wavelength of the visible light can be 600 nm to 780 nm, is preferably 650 nm to 770 nm, is more preferably 680 nm to 760, and is particularly preferably 700 nm to 750 nm.

In an embodiment of the above invention, the light source can be an LED. The LED can be housed in the emission part. From a viewpoint of allowing light to easily pass to the outside of a lumen even when the emission part is directed to any direction inside the lumen, the emission part is preferably formed of a transparent material. Although not limited, the emission part can be formed of a transparent resin material or the like. As the transparent resin material, for example, acrylic resin, urethane resin, melamine resin, alkyd resin, paraxylylene resin, siloxane polymer, organic silane condensate, or the like can be used. From a viewpoint of enhancing diffusibility of light, diffusion particles can be dispersed to be disposed in the emission part. As the diffusion particles, for example, powder of silica or quartz can be used.

Although not limited, thread is provided so as to form a ring and is fastened to the outer periphery of a cover part, so that the emission marker can be set to the clip for an endoscope. The emission marker can be inserted into a forceps channel of an endoscope along with the clip for an endoscope to be indwelled in the tumor vicinity.

In an embodiment of the above invention, the emission marker further has a perforation part. The perforation part may be provided at a site where the emission marker is perforated. The perforation part may be continuously provided to be adjacent to the emission marker. The perforation part may be connected to at least one end of the emission marker and be provided so as to wrap around the emission marker with a predetermined gap therebetween. The number of the perforation parts may be one, or may be a plural number. In a case where the perforation part is provided at the site where the emission marker is perforated, the perforation part can be provided at a central part of the emission marker or at an outside position deviated from the central part. The perforation part is preferably provided at the outside position deviated from the central part of the emission marker, in order that while the emission marker is set to a clip for an endoscope or the like, and its opening/closing arm is closed, the emission marker can be inserted into a forceps channel or the like. The gap can be provided in a range so as to enable insertion into the clip for an endoscope.

In an embodiment of the above invention, the cover part is formed of a polymer base agent. Consequently, the base part, the coil, the emission part and the like can be protected from exposure to gastric juices or intestinal juices, and therefore safe utilization in short to long indwelling is possible. As the polymer base agent, silicone, polyurethane, or the like can be used. In a case where the perforation part is provided at the site where the emission marker is perforated, the perforation part can be also formed of the polymer base agent.

In an embodiment of the above invention, the emission marker has a size enabling insertion into a forceps channel of an endoscope. Additionally, in a state where the emission marker is set in the clip for an endoscope, the emission marker and the clip for an endoscope may have a size enabling insertion into the forceps channel of the endoscope. The size of the emission marker is reduced up to such a degree as to be able to be inserted into the forceps channel of the endoscope, so that clinical usefulness is enhanced, and the emission marker is formed in such a shape as to be easily indwelled under the endoscope. While being connected to the clip for an endoscope, the emission marker is inserted into the forceps channel of the endoscope by a publicly known method. This perforation part is held by a claw part of the clip for an endoscope, so that the emission marker can be indwelled in the vicinity of a lesion in endoscopic surgery. Although not limited, the emission marker may be integrated by being incorporated into a part of the clip for an endoscope.

In an embodiment of the above invention, the inner diameter of the forceps channel is 2 mm to 10 mm. In a case where a digestive tract endoscope is used, the inner diameter of the forceps channel is preferably 5 mm or less, and is more preferably 3 mm or less. Accordingly, the size of the emission marker is preferably smaller than the inner diameter of the forceps channel.

In an embodiment of the above invention, the emission marker can be formed in a cylindrical shape, a rectangular parallelepiped shape, a cubic shape, or the like. The maximum diameter of a surface orthogonal to the longitudinal direction of the emission marker is preferably 10 mm or less, is more preferably 5 mm or less, is particularly preferably 3 mm or less, and is most preferably 2 mm or less. Additionally, the maximum diameter of the surface orthogonal to the longitudinal direction of the emission marker can be 2 mm to 2.9 mm, and is preferably 2.2 mm to 2.5 mm.

In an embodiment of the above invention, the emission marker is indwelled in the tumor vicinity. When the indwelled position is too far from the tumor, identification of a lesion site is unclear, and when the indwelled position is right above the tumor, a tumor tissue may be damaged, which is not preferable. The indwelled position is not limited as long as the identification of the lesion site is clear. For example, the indwelled position is preferably 3 cm or less from a tumor, is more preferably 2 cm or less, and is further more preferably 1 cm or less. In order to identify the position of a tumor, at least two emission markers can be indwelled in the vicinity of the tumor. For example, the emission markers can be indwelled at both ends of the tumor in the longitudinal direction of the lumen.

In an embodiment of the above invention, a memory is provided in a base part of the emission marker. Identification information can be recorded in the memory, and a detector (e.g., reader/writer) described below can read/write the information in the memory.

The present invention can be a kit including the emission marker, and the clip for an endoscope.

The present invention relates to a detector for detecting, from outside of a lumen, an emission marker indwelled in the lumen, the detector including a detection unit having an antenna that acts with a coil of the emission marker.

In an embodiment of the above invention, the detection unit may further have a support part provided in the detection unit. The support part can be rigid or flexible. Although not limited, in a case where the support part is rigid, the support part can be a bar-shape. In a case where the support part is flexible, the support part can be freely bent, and the bent state can be preferably held.

In an embodiment of the above invention, the antenna is a coil type antenna. The emission marker a magnetic flux or a radio wave from the detector acts on the emission marker, so that a current is generated by electromagnetic induction or resonance. The current is supplied to the emission part of the emission marker, and the emission marker emits visible light.

In an embodiment of the above invention, the detector further has a power supply.

In an embodiment of the above invention, in a case where the emission marker has a memory, the detector further preferably has a monitor. Information read out from the memory can be displayed on the monitor of the detector.

In an embodiment of the above invention, the emission marker may have a memory, and may have a function as an RF tag.

In an embodiment of the above invention, the emission marker can be an electromagnetic induction system passive tag, or an electric wave system passive tag.

In a case where the emission marker has the memory, the emission marker may further have a control circuit that reads/writes information to the memory.

In an embodiment of the above invention, at least the detection unit and the support part can be inserted into a laparoscope port.

In an embodiment of the above invention, the inner diameter of the laparoscope port is 2 mm to 20 mm.

In an embodiment of the above invention, at least the detection unit and the support part are formed to be high-temperature and high-pressure steam sterilizable.

In an embodiment of the above invention, at least one part of each of the detection unit and the support part is made of oxygen free copper, silicone, polycarbonate, polypropylene, polyolefin, polysulfone, polyethylene terephthalate, polybutylene terephthalate, Teflon (registered trademark), rubber-like polymer, or polyvinyl chloride. Although not limited, a base plate where the antenna and the reader are disposed in the detection unit is covered by a high-temperature and high-pressure steam sterilizable material such as those above, so that the body of the detector can be formed.

Although not limited, in the support part, the covering material of a wire can be formed of a high-temperature and high-pressure steam sterilizable material such as those above. From a viewpoint of prominently exerting an effect of the present invention, at least one part of each of the detection unit and the support part are preferably made of oxygen free copper or silicone. In a case where constant flexibility is given to the support part of the detector, an insulating film having flexibility such as films of silicone and polyvinyl chloride is preferably used.

According to the present invention, it is possible to provide an RF tag marker and an emission marker capable of identifying an accurate lesion site and an accurate excisional range, and a detector for the same.

DETAILED DESCRIPTION OF THE PREFERRED EMBODIMENT

Hereinafter, the present invention will be described with reference to the drawings.

In the following description, the drawings based on the following embodiments are schematic diagrams, relations between the thicknesses and the widths of respective parts, ratios of the thicknesses of the respective part, and the like are sometimes different from actual relations and ratios. Additionally, relations and ratios of dimensions between the drawings may include different parts.

IC Tag Marker

Figure 1:
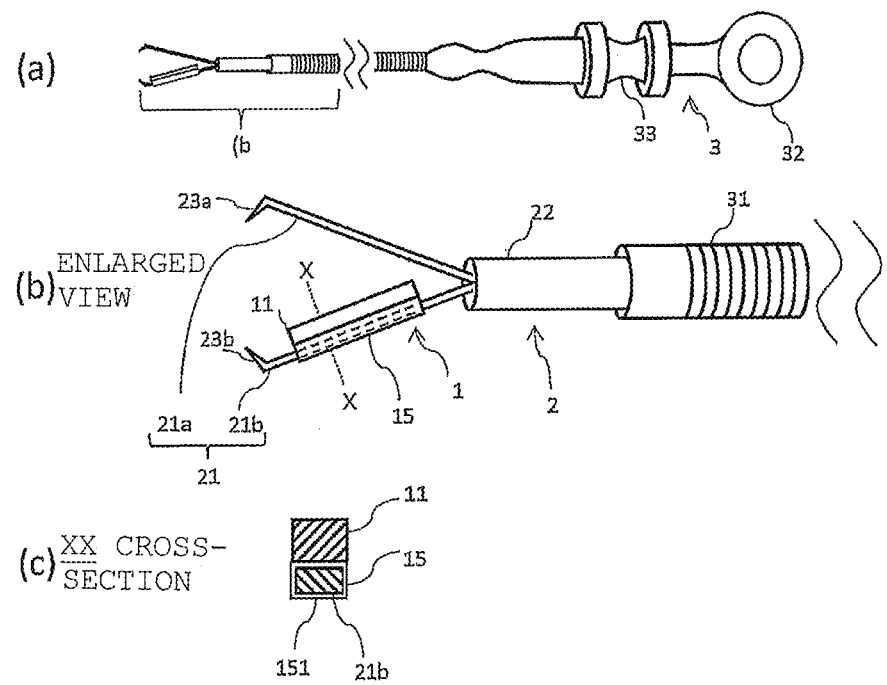
FIG. 1 is a plan view illustrating an entire configuration in a case where an IC tag marker is inserted into a clip for an endoscope.
Figure 2A:
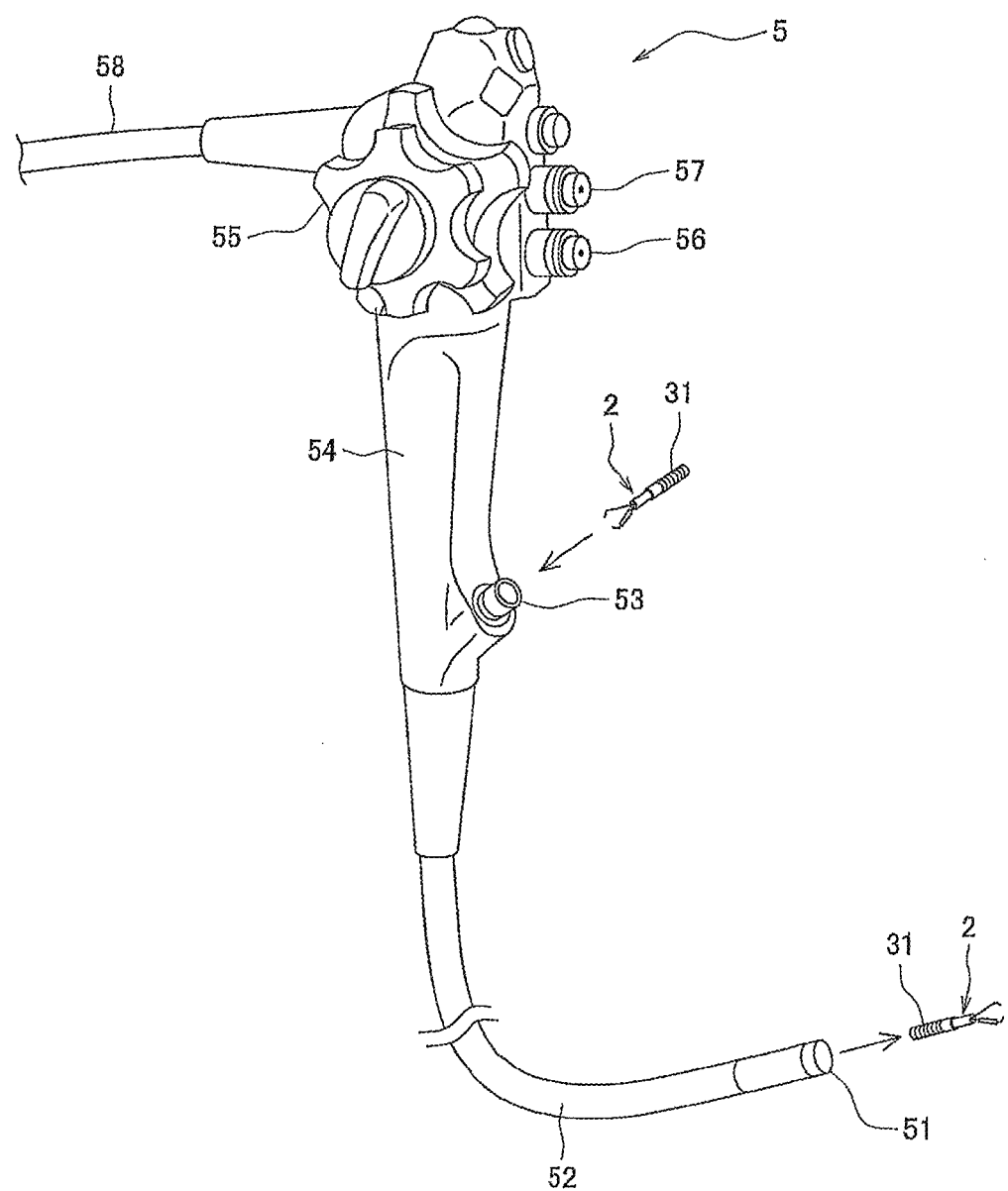
FIGS. 2A-2B show a diagram illustrating a series of states where the IC tag marker is inserted into the clip for an endoscope to be indwelled in the tumor vicinity.
Figure 2B:
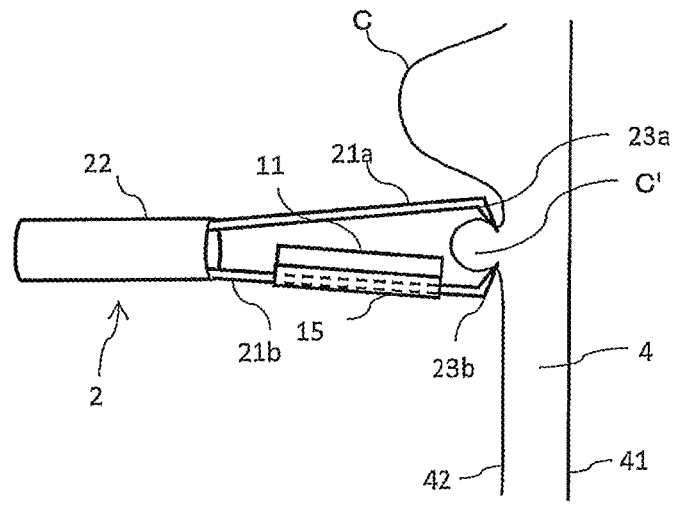

As illustrated in FIG. 1, and FIGS. 2A-2B, an IC tag marker 1 of the present invention has a body 11, and a perforation part 15 provided in body 11. In this embodiment, the IC tag marker 1 is used by being indwelled in a lumen.

In this specification, the lumen means the inside of an organ having a tract such as a small intestine and a large intestine. The organ having a lumen is not particularly limited, but preferably a digestive tract from a viewpoint of being capable of giving treatment by an endoscope, more preferably an esophagus, a stomach, a duodenum, a small intestine, a large intestine, a colon, or a rectum, and furthermore preferably a stomach, a large intestine, a colon, or a rectum.

Figure 3:
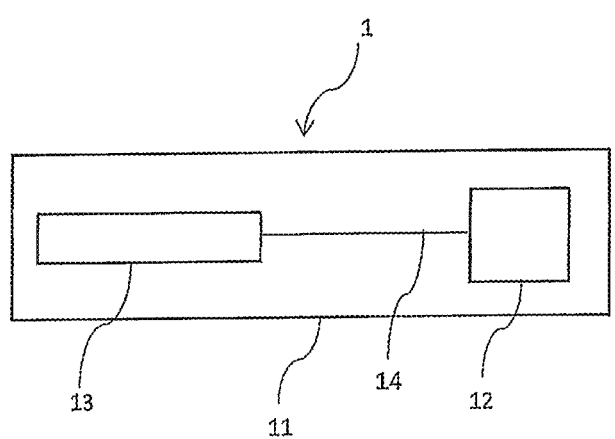
FIG. 3 is a diagram illustrating an example of the IC tag marker.

As illustrated in FIG. 3, the IC tag marker 1 may have an IC chip 12 and an antenna 13 inside the body 11 of the IC tag marker 1. In this specification, an RFID is an abbreviation for Radio Frequency Identification, and means a system for reading and writing data recorded in an IC tag marker by use of radio waves or the like in a non-contact manner. The IC tag marker 1 can read and write identification information recorded in a memory of the IC chip 12 by use of a system of the RFID.

The IC chip 12 may have a memory that records identification information. The identification information is not limited, and examples of the identification information include names of patients, sexes, privacy information of patients such as ages, past medical histories and/or current medical states (past histories) of the patient, patient reference numbers, names of operators, names of hospitals, dates of surgery, organ names, information of indwelled positions, and the like. Additionally, the memory of the IC chip 12 can write data at any time, and therefore can also record how an excised tissue sample having the IC tag marker 1 indwelled therein is preserved, how the tissue sample is treated, and the like, and can secure traceability.

The antenna 13 is preferably a coil type antenna from a viewpoint of being capable of obtaining induced electromotive force by radio waves or an induction field generated by acting with a detector 6 described below, and running.

The IC chip 12 may have a control circuit. The control circuit is connected between a coil and the memory, so that induced electromotive force generated from the coil can be controlled.

As the IC tag marker 1, any of a passive tag, an active tag, and a semi-active tag formed by combining the both can be used. However, the passive tag is preferable from a viewpoint of being capable of downsizing the body 11 of the IC tag marker 1 without the need for incorporating a battery. In a case where the IC tag marker 1 is used as the passive tag, the IC tag marker can run while using radio waves from an antenna 62 described below, or the like, as an energy source, and identification information recorded in the memory of the IC chip 12 can be read and written by a reader/writer 61.

A frequency band used in the IC tag marker 1 is not particularly limited as long as the frequency band is a range in which an effect of the present invention is obtained. However, a frequency band standardized in ISO/IEC is preferable. For example, 130 to 135 KHz band, 13.56 MHz band, 2.45 GHz band, 860 MHz to 960 MHz band, 433 MHz band, or the like can be used. Among these, in a case where the IC tag marker 1 is used as the passive tag, a frequency band used in the IC tag marker 1 is preferably 130 to 135 KHz band or 13.56 MHz band. The frequency band used in the IC tag marker 1 is set to 130 to 135 KHz band or 13.56 MHz band, so that a frequency is relatively low, and therefore the IC tag marker 1 can be used in a condition of being hardly influenced by moisture inside and outside the lumen. The frequency band used in the IC tag marker 1 is set to 130 to 135 KHz band or 13.56 MHz band, so that the IC tag marker 1 can be used without radio interference with existing systems of 2.45 MHz band used in a wireless LAN or the like, existing systems of 860 MHz to 960 MHz band used in a portable telephone or the like, and the like.

As illustrated in FIG. 1a, a treatment tool 3 for an endoscope has a support part 32 and a slider 33 on a proximal side. Additionally, the treatment tool 3 for an endoscope has a protective sheath 31 on a distal side. An operator holds the support part 32 to operate the slider 33, so that the operator can operate an apparatus mounted on a tip part of the protective sheath 31.

FIG. 1b is an enlarged view of the tip part of the protective sheath 31. A clip 2 for an endoscope has a clip unit 22 and an opening/closing arm 21. In the example illustrated in FIG. 1b, the opening/closing arm 21 is composed of a pair of two claw parts 21a and 21b. Respective distal ends of the claw parts 21a and 21b have protrusions 23a and 23b protruding inward of the clip 2 for an endoscope. The clip 2 for an endoscope is mounted on the tip of the protective sheath 31 of the treatment tool 3 for an endoscope, and the pair of claw parts 21a and 21b opens and closes by operation of the slider 33 of the treatment tool 3 for an endoscope.

The perforation part 15 of the IC tag marker 1 can be inserted around at least one of the pair of claw parts 21a and 21b in the clip 2 for an endoscope. In the example illustrated in FIG. 1b, the perforation part 15 of the IC tag marker 1 is inserted around the claw part 21b. The respective distal ends of the claw parts 21a and 21b have the protrusions 23a and 23b, and therefore the IC tag marker 1 hardly drops. Additionally, in order to prevent the IC tag marker 1 from dropping from the claw part 21b due to the operation during surgery, the operation is possible in a state where the opening/closing arm 21 is closed during surgery. From a viewpoint of performing operation in a state where the opening/closing arm 21 is closed during surgery, or the like, the longitudinal length of the IC tag marker 1 is preferably set to be shorter than the length of the claw part 21b. Additionally, from a viewpoint of preventing the IC tag marker 1 from dropping from the distal end of the claw part 21b, the longitudinal length of the IC tag marker 1 is preferably set to be shorter than the protrusion 23b located at the distal end of the claw part 21b.

FIG. 1c illustrates the X-X cross-section in FIG. 1b. In the example illustrated in FIG. 1c, the perforation part 15 of the IC tag marker 1 is provided outside the above body 11 while being adjacent to the body 11 of the IC tag marker 1. The perforation part 15 may include a film 151 and the like, the claw part 21b is inserted into the inside of the film. In order to prevent the IC tag marker 1 from dropping from the claw part 21b due to the operation during surgery, the inner diameter of the perforation part 15 can be set in accordance with the size of the claw part 21b, or can be set so as to expand and contract in accordance with the size of the claw part 21b. With such a configuration, various shaped clip for an endoscopes can be used as the clip 2 for an endoscope.

In the example illustrated in FIG. 1b and FIG. 1c, the body 11 of the IC tag marker 1 is disposed inside the opening/closing arm 21 of the clip 2 for an endoscope. More specifically, the body 11 of the IC tag marker 1 is disposed inward of the pair of claw parts 21a and 21b. With such a configuration, as illustrated in FIG. 2a, when the clip 2 for an endoscope is inserted into an inlet 53 of a forceps channel of an endoscope 5 while being mounted on a tip of the protective sheath 31 of the treatment tool 3 for an endoscope, the body 11 of the IC tag marker 1 does not hinder. However, when the body 11 is formed so as not to hinder when the when IC tag marker 1 is inserted into the forceps channel of the endoscope 5, the body 11 of the IC tag marker 1 can be set outside the opening/closing arm 21 of the clip 2 for an endoscope.

As illustrated in FIG. 2a, while the IC tag marker 1 is inserted around the claw part 21b, the clip 2 for an endoscope mounted on the tip of the protective sheath 31 of the treatment tool 3 for an endoscope is inserted into the forceps channel of the endoscope 5 to be delivered to a lesion site.

More specifically, the clip 2 for an endoscope mounted on the tip of the protective sheath 31 of the treatment tool 3 for an endoscope is inserted from the inlet 53 of the forceps channel of the endoscope 5 to be delivered to the lesion site through an outlet 51 of the forceps channel. As illustrated in FIG. 2b, the operator confirms the lesion site to determine a site to be excised, and thereafter puts the protrusions 23a and 23b of the claw parts 21a and 21b of the clip 2 for an endoscope to the lumen inside 42 at a desired site to operate the treatment tool 3 for an endoscope, thereby closing the claw parts 21a and 21b. Although not limited, it is preferable that the claw parts 21a and 21b are fixed while being closed, by further operation of the treatment tool 3 for an endoscope, and the clip 2 for an endoscope is separated from the protective sheath 31, so that the IC tag marker 1 is indwelled.

A site where the IC tag marker 1 is indwelled can be determined by a type of a disease, an organ or a site where the disease exists, and other patient's state. For example, in a case where a site suspicious of cancer is excised, the IC tag marker 1 can be indwelled in the vicinity of the site suspicious of cancer, from a viewpoint of avoiding damage to a tissue sample to be excised, or the like. The IC tag marker 1 can be also indwelled in the vicinity of a site to be excised, from a viewpoint of possible scattering of the cancer cell into the lumen or to a blood vessel, or the like, in a case where cancer is excised, when a cancer tissue is damaged by the claw parts 21a and 21b of the opening/closing arm 21, for example. FIG. 2b illustrates a state where the IC tag marker 1 is indwelled in the vicinity C' of a bulge by a tumor C while being inserted into the clip 2 for an endoscope. In this case, when the lumen is a digestive tract, the IC tag marker 1 can be indwelled in a mucosa part in the lumen inside 42.

Figure 4:
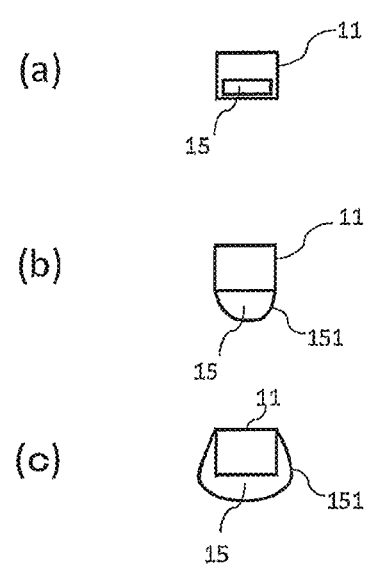
FIG. 4 is a plan view illustrating an example of a perforation part of the IC tag marker.

FIG. 4 illustrates various embodiments of the perforation part 15 of the IC tag marker 1. More specifically, in FIG. 4a, the perforation part 15 is provided in a site where the body 11 of the IC tag marker 1 is perforated. In FIG. 4a, the perforation part 15 exists at an outside position deviated from a central part of the body 11, so that the IC chip 12 and the antenna 13 can be disposed on another side. With such a configuration, the IC tag marker 1 can be inserted around the claw part 21b of the opening/closing arm 21 such that the IC chip 12 and the antenna 13 are disposed on the inside of the opening/closing arm 21, and the IC tag marker 1 hardly hinders when the IC tag marker 1 is inserted into the forceps channel of the endoscope 5.

In FIG. 4b, the perforation part 15 is continuously provided to be adjacent to the body 11 of the IC tag marker 1. In FIG. 4c, the perforation part 15 is provided so as to wrap around the above body with a predetermined gap therebetween. In a case where the perforation part 15 is located outside the body 11, the perforation part 15 can be formed of a biocompatible material. For example, in a case where the perforation part 15 is formed of a film material 151, the cylindrical film material 151 can be provided on side surfaces of the body 11 of the IC tag marker 1 by a publicly known method.

Another Embodiment of IC Tag Marker

The IC tag marker 1 can be formed so as not to have the perforation part 15. The perforation part 15 has a role as a connecting part when connecting the clip 2 for an endoscope or the like for assisting indwelling to a lumen, and therefore, for example, in a case where the IC tag marker is incorporated into the clip 2 for an endoscope itself, the perforation part 15 is unnecessary. Accordingly, in another embodiment of the present invention, it is possible to provide a clip for an endoscope which is indwelled in a lumen, and has an RF tag marker having an antenna and an IC chip.

The embodiment in which the IC tag marker is attached to the clip for an endoscope is not limited as long as an effect of the present invention is exerted. However, the IC tag marker can be provided in an opening/closing arm 21 or a clip unit 22 of the clip for an endoscope. In a case where the IC tag marker is provided in the clip for an endoscope, an incorporated site is not limited. For example, the IC tag marker can be provided on the inside or the outside of the clip unit 22 of the clip 2 for an endoscope illustrated in FIG. 2b. The clip for an endoscope provided with the IC tag marker has preferably a size enabling insertion into a forceps channel of an endoscope. In the IC tag marker, a configuration and operation of the clip for an endoscope which does not have the perforation part 15 are similar to the above.

Detector for IC Tag Marker

Figure 5:
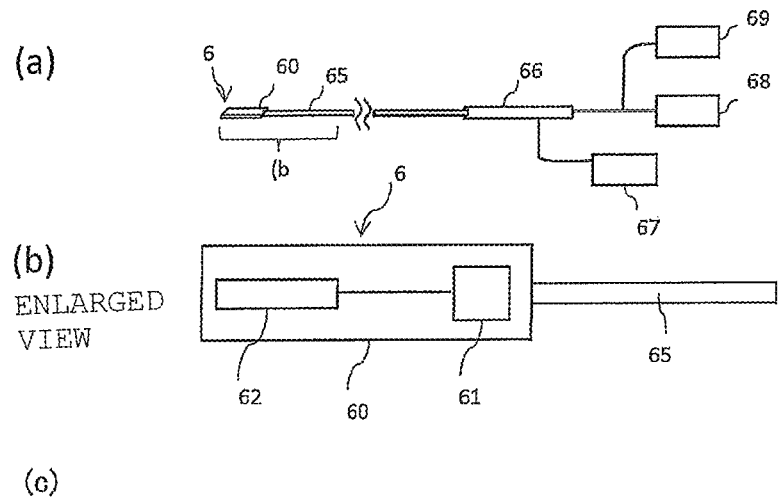
FIG. 5 is a plan view illustrating an example of a detector and use therefor.
Figure 5:
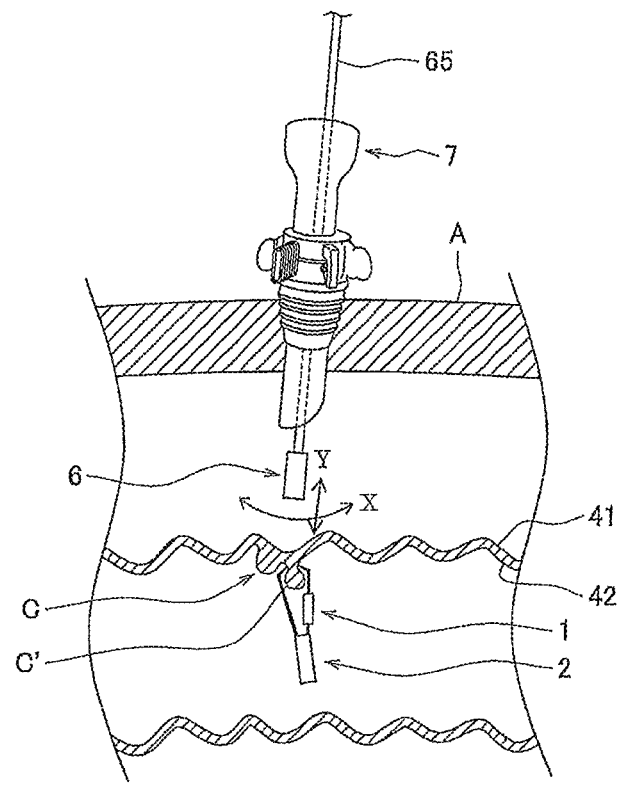

As illustrated in FIG. 5b, the detector 6 includes a detection unit 60 having the antenna 62 capable of communicating with the IC tag marker 1, and a reader 61. Additionally, the detector 6 may have a support part 65 extending from the detection unit 60. In this embodiment, the IC tag marker 1 indwelled in the lumen can be detected from the outside of the lumen by using the detector 6. More specifically, in laparoscopic surgery, the detector 6 is used, so that the IC tag marker 1 indwelled in the lumen can be detected from a serosal surface of an intestinal tract, and an excisional range can be identified.

The support part 65 may have an operation unit 66 on a proximal side. An operator can hold this operation unit 66 to operate the position or the direction of the detector 6. Additionally, the support part 65 may be connected to a power supply 67 on a proximal side. Furthermore, the support part 65 may have a notification unit such as a sound generation unit 68 and/or a monitor 69 on a proximal side. The detector 6 has the notification unit, so that detection of the IC tag marker 1 can be notified to the operator by sound, light, and screen display. Although not limited, the detector 6 can be set so as to emit sound from the sound generation unit 68, when the detector 6 approaches the IC tag marker 1 from the serosal surface of the intestinal tract, and approaches up to a constant distance.

To the detector 6, power is supplied from the power supply 67. Additionally, in the detector 6, the reader 61 reads a signal received from the IC tag marker 1 by the antenna 62. In a case where the IC tag marker 1 indwelled in the lumen is detected from the outside of the lumen, the detector 6 approaches the IC tag marker 1, so that the antenna 62 can detect a signal from the IC tag marker 1.

A range in which the detector 6 can detect the IC tag marker 1 is different depending on types and performance of the IC tag marker 1 and the antenna 62. Although not limited, for example, in a case where the IC tag marker 1 is used as a passive tag, even when moisture or a wall surface of an intestinal tract or the like is interposed, the range can be within at least 5 cm. From a viewpoint of accurately detecting the position of the IC tag marker 1, the detection range is preferably within 5 cm or less, and more preferably within 3 cm or less. Additionally, the detection range can be 0 cm or more (state where the IC tag marker 1 and the antenna 62 are in contact).

The power supply 67 or the notification unit may be incorporated in the operation unit 66. In a case where the power supply 67 is incorporated in the operation unit 66, a battery such as a rechargeable battery can be disposed in the operation unit 66. Although not limited, the power supply 67 or the sound generation unit 68 is incorporated in the operation unit 66, so that the detector 6 can be used in a cordless manner.

The detection unit 60 in the detector 6 may further have a writer 61. In this case, information can be written in the memory of the IC chip 12 by the writer 61. For example, in a case where an excised tissue sample is stored, information such as dates and times of surgery, patient reference numbers, organ names, information of indwelled positions, storage places, and test results can be written in the memory of the IC chip 12.

As illustrated in FIG. 5c, a laparoscope port 7 is used by being inserted into an abdominal wall A in laparoscopic surgery. The detector 6 is inserted into the laparoscope port 7 to be delivered in the abdominal cavity. The operator operates the detector 6 by a publicly known method to detect the position of the IC tag marker 1 indwelled in the lumen. The detector 6 can approach the IC tag marker 1 along the lumen in the X direction to detect the IC tag marker 1. Additionally, the detector 6 can approach the IC tag marker 1 from a place away from the lumen in the Y direction to detect the IC tag marker 1. In the example illustrated in FIG. 5c, the IC tag marker 1 is indwelled in the vicinity C' of the tumor C, and the detector 6 detects the IC tag marker 1 from the serosal surface (namely, lumen outside 41) of the intestinal tract, so that it is possible to identify the excisional range.

The detector 6 may be formed to be high-temperature and high-pressure steam sterilizable. In this case, the detector 6 is useful for enabling safely repeated utilization.

In a case where the IC tag marker 1 does not have the perforation part, a detector that detects a clip for an endoscope indwelled in a lumen from the outside of the lumen, and has a detection unit having an antenna and a reader can be provided as another embodiment. The specific configuration and operation of the detector is similar to the above.

Emission Marker

Figure 6:
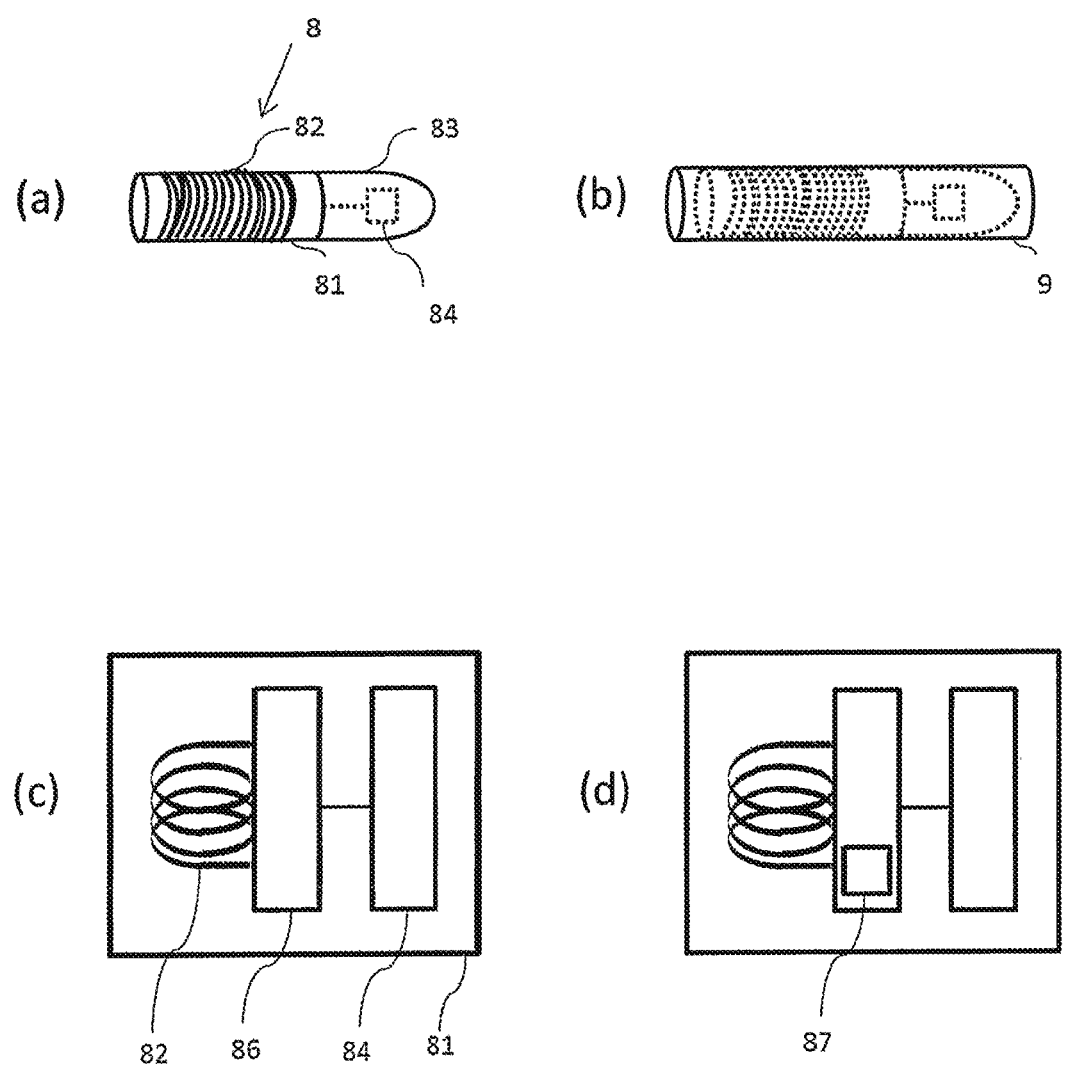
FIG. 6 is a schematic diagram illustrating an example of an emission marker.

As illustrated in FIG. 6a, an emission marker 8 of the present invention has a base part 81, a coil 82 wound around the base part 81, and an emission part 83 electrically connected to the coil 82. The emission part 83 may be provided at an end of the base part 81. The emission part 83 has a light source, and a current is supplied from the coil 82 to this light source. The obtained current can be adjusted by the number of turns of the coil 82. The winding diameter of the coil 82 is adjusted to have such a size as to enable the emission marker 8 to be inserted into the forceps channel of the endoscope.

From a viewpoint of being able to emit light even with a small current, the light source used in the emission part 83 is preferably an LED 84. As the light source, in addition to the LED, a semiconductor laser, and an SLD (super luminescent diode) may be used. In the emission part 83, the LED 84 is connected to the coil 82. The LED 84 can be disposed at any position inside the emission part 83. However, from a viewpoint of more efficiently diffusing light, the central part of the emission part 83 is preferable. As long as the size is such a size as to enable the emission marker 8 to be inserted into the forceps channel of the endoscope, the emission marker 8 may include a plurality of the coils 82 and a plurality of the LEDs 84.

As illustrated in FIG. 6b, in the emission marker 8, the base part 81, the coil 82, and the emission part 83 are covered with a cover part 9 formed of a polymer base agent. In a case where the coil 82 is wound around an outside surface of the base part 81, there is a possibility that the coil 82 may corrode due to being exposed to gastric juices or intestinal juices during surgery or during indwelling. Outside surfaces of the base part 81, the coil 82, and the emission part 83 are covered with the cover part 9, so that the base part 81, the coil 82, and the emission part 83 can be protected from gastric juices, intestinal juices, or physical stimuli.

FIG. 6c and FIG. 6d each are a diagram of a conceptually illustrated circuit of the emission marker 8. In the emission marker 8, the coil 82 is provided so as to be wound around the base part 81, and has the emission part 83 electrically connected to the coil 82. The control circuit 86 may be connected between the coil 82 and the emission part 83. As the detector 6 approaches, a generating current increases. With this, light emitted from the emission part 83 is strengthened. Additionally, as the detector 6 gets away, the generating current decreases. With this, light emitted from the emission part 83 is weakened. The control circuit 86 may include a constant current circuit. The control circuit 86 may directly supply a current generated in the coil 82 to the light source. Additionally, when the current generated in the coil 82 is a threshold value within a predetermined range, the control circuit 86 may supply a current equivalent to the threshold value. A plurality of the threshold values (lower limit to upper limit) within the predetermined range may be set.

Figure 7:
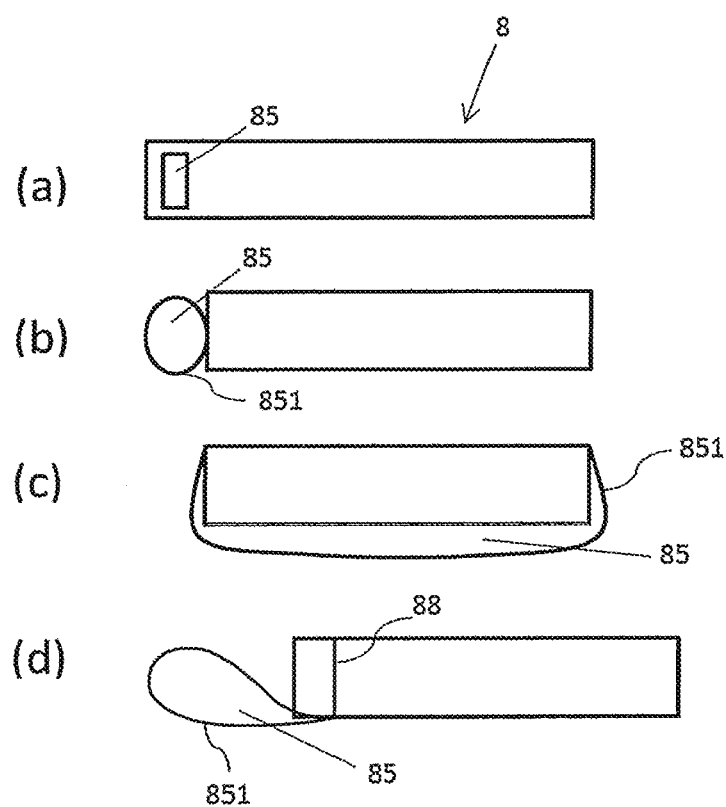
FIG. 7 is a plan view illustrating an example of a perforation part of the emission marker.

FIG. 7 illustrates various embodiments of a perforation part 85 of the emission marker 8. More specifically, in FIG. 7a, the perforation part 85 is provided at a site where the emission marker 8 is perforated. In FIG. 7a, the perforation part 85 exists at an outside position deviated from the central part of the emission marker 8. In FIG. 7b, the perforation part 85 is continuously provided to be adjacent to the emission marker 8. In FIG. 7c, the perforation part 85 is provided so as to wrap around the above base part with a predetermined gap between the emission marker 8 and the perforation part 85. In a case where the perforation part 85 is located outside the emission marker 8, the perforation part 85 can be formed of a biocompatible material. For example, in a case where the perforation part 85 is formed of a film material 851, the cylindrical film material 851 can be provided on side surfaces of the emission marker 8 by a publicly known method. With such a configuration, when mounted on the clip 2 for an endoscope, the emission marker 8 and the clip 2 for an endoscope are linearly disposed in series, thereby enabling insertion into the forceps channel of the endoscope 5. In FIG. 7d, a thread 88 used in surgery is fastened to the emission marker 8, and this thread 88 is provided so as to form a ring 851, thereby forming the perforation part 85.

The emission marker 8 can be formed without providing the perforation part 85. The perforation part 85 has a role as a connecting part used when the clip 2 for an endoscope or the like for assisting indwelling to a lumen is connected. Accordingly, for example, in a case where the emission marker 8 is incorporated in the clip 2 for an endoscope itself, the perforation part 85 is unnecessary. In another embodiment of the present invention, it is possible to provide a clip for an endoscope for being indwelled in a lumen, the clip for an endoscope having an emission marker having a coil and an emission part.

Figure 8:
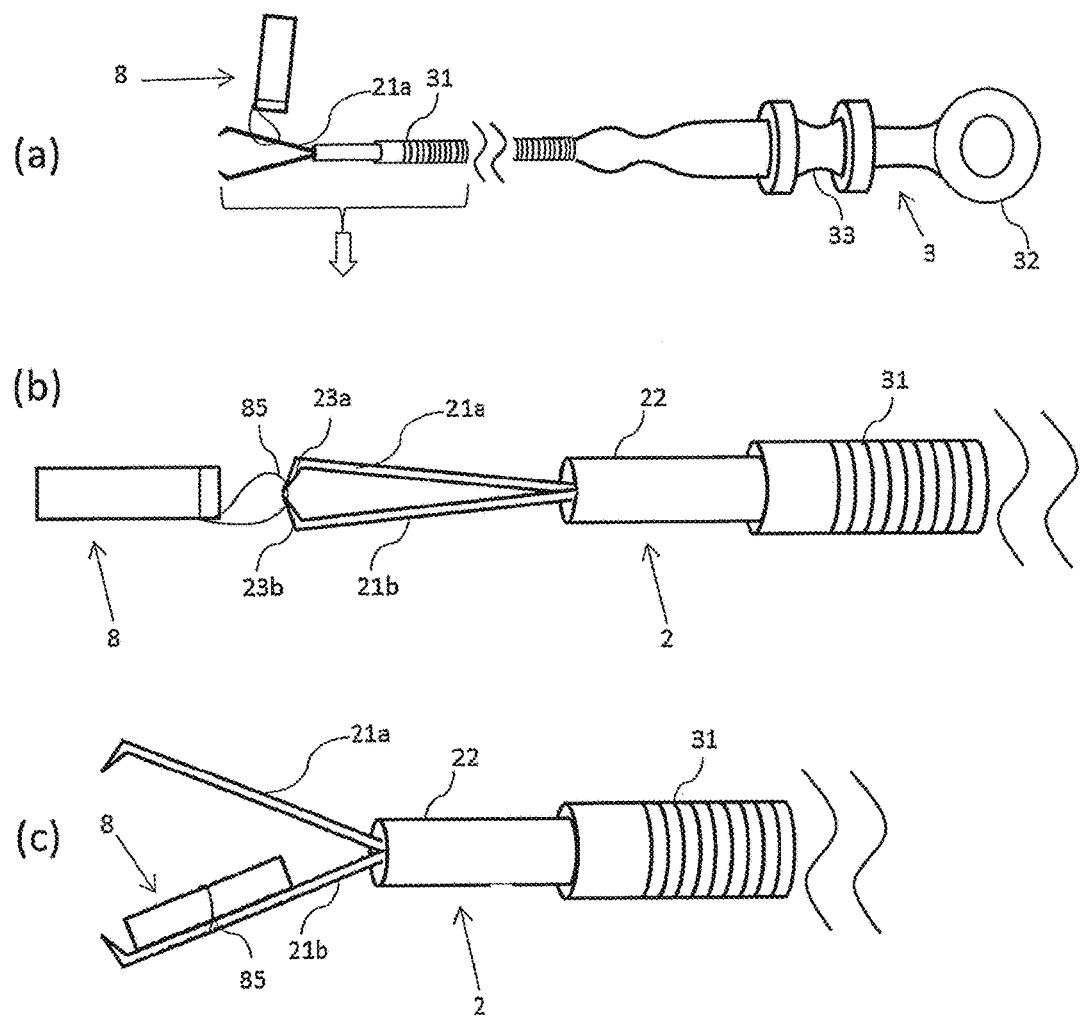
FIG. 8 is a schematic diagram illustrating an entire configuration in a case where the emission marker is inserted into the clip for an endoscope.

As illustrated in FIG. 8a, a treatment tool 3 for an endoscope has a support part 32 and a slider 33 on a proximal side. Additionally, the treatment tool 3 for an endoscope has a protective sheath 31 on a distal side. An operator holds the support part 32 to operate the slider 33, so that the operator can operate a clip 2 for an endoscope mounted on a tip part of the protective sheath 31. In FIG. 8a, a perforation part 85 of an emission marker 8 is inserted around a claw part 21*a* of the clip 2 for an endoscope.

The perforation part 85 of the emission marker 8 can be inserted around at least one of a pair of claw parts 21*a* and 21*b* in the clip 2 for an endoscope. Respective distal ends of the claw parts 21*a* and 21*b* have protrusions 23*a* and 23*b*, and therefore the emission marker 8 hardly drops. In the example illustrated in FIG. 8*b*, the perforation part 85 of the emission marker 8 is inserted around the claw part 21*a*, and thereafter an opening/closing arm 21 is closed, so that the emission marker 8 and the clip 2 for an endoscope are linearly disposed in series. The emission marker 8 and the clip 2 for an endoscope are thus disposed, so that the emission marker 8 is easily inserted into a forceps channel of an endoscope. Like the example illustrated in FIG. 8*c*, the emission marker 8 may be disposed on the inside of the opening/closing arm 21 of the clip 2 for an endoscope. In a case where the emission marker 8 is disposed inside the opening/closing arm 21 of the clip 2 for an endoscope, the perforation part 85 may be formed of a thread used in surgery, and the emission marker 8 may be set in the claw part 21*b* of the clip 2 for an endoscope.

In a state where the emission marker 8 is inserted around the claw part 21, the clip 2 for an endoscope mounted on the tip of the protective sheath 31 of the treatment tool 3 for an endoscope can be inserted into the forceps channel of the endoscope to be delivered to a lesion site. A method for the operation of the endoscope and indwelling is similar to the method described for the IC tag marker 1 in FIG. 2*a* and FIG. 2*b*.

Figure 9:
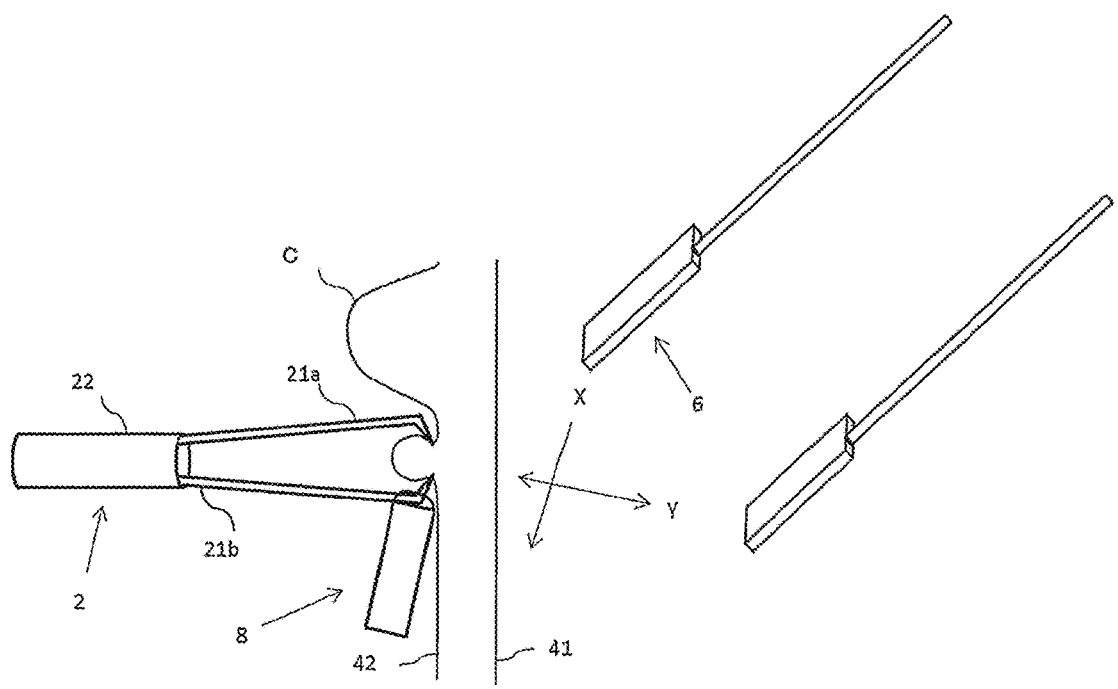
FIG. 9 is a schematic diagram illustrating an example of the emission marker indwelled in the tumor vicinity, and a detector therefor.

A site where the emission marker 8 is indwelled can be determined by a type of a disease, an organ or a site where the disease exists, and other patient's state. For example, in a case where a site suspicious of cancer is excised, the emission marker 8 can be indwelled in the vicinity of the site suspicious of cancer, from a viewpoint of avoiding damage to a tissue sample to be excised, or the like. The emission marker 8 can be also indwelled in the vicinity of a site to be excised, from a viewpoint of possible scattering of the cancer cell into the lumen or to a blood vessel, or the like, in a case where cancer is excised, when a cancer tissue is damaged by the claw parts 21*a* and 21*b* of the opening/closing arm 21, for example. FIG. 9 illustrates a state where the emission marker 8 is indwelled in the vicinity C' of a bulge by a tumor C while being inserted into the clip 2 for an endoscope. In this case, when the lumen is a digestive tract, the emission marker 8 can be indwelled in a mucosa part in the lumen inside 42.

Another Embodiment of Emission Marker

The emission marker may be used in such a mode as to be incorporated in a clip for an endoscope. Accordingly, in another embodiment of the present invention, it is possible to provide a clip for an endoscope for being indwelled in a lumen, the clip for an endoscope having a coil, and an emission part electrically connected to the coil, wherein the emission part has an emission marker having a light source for emitting visible light. The coil may be provided by being wound around a part of the clip for an endoscope.

The mode in which the emission marker is incorporated in the clip for an endoscope is not limited as long as an effect of the present invention is exerted. However, the emission marker can be provided in an opening/closing arm 21 or a clip unit 22 of the clip for an endoscope. The emission marker can be provided, for example, on the inside or the outside of the clip unit 22 of the clip 2 for an endoscope illustrated in FIG. 2*b*. The clip for an endoscope provided with the emission marker has preferably a size enabling insertion into a forceps channel of an endoscope.

In a case where the emission marker is incorporated in the clip for an endoscope, the emission part may be provided at an end of the clip for an endoscope. In the clip for an endoscope having the emission marker, at least the coil and the emission part may be covered with a cover part formed of a polymer base agent. Other configurations and an operation method of the emission marker incorporated in the clip for an endoscope are similar to the above description of the emission marker.

Detector for Emission Marker

As illustrated in FIG. 9, the emission marker 8 indwelled in the lumen inside 42 is detected from the lumen outside 41 (serosal surface of an intestinal tract) by a detector 6. A coil type antenna 62 of the detector 6 approaches, a current is generated in the coil 82 by electromagnetic induction, and an LED 84 electrically connected to the coil 82 emits light. The detector 6 can approach the emission marker 8 along the lumen in the X direction to emit the LED 84. Additionally, the detector 6 can approach the emission marker 8 from a place away from the lumen in the Y direction to emit the LED 84.

A frequency band used in the emission marker 8 is not particularly limited as long as the frequency band is in a range in which an effect of the present invention is obtained. However, a frequency band standardized in ISO/IEC is preferable. For example, 130 to 135 KHz band, 13.56 MHz band, 2.45 GHz band, 860 MHz to 960 MHz band, 433 MHz band, or the like can be used. The frequency band used in the emission marker 8 is preferably 130 to 135 KHz band or 13.56 MHz band. The frequency band used in the emission marker 8 is set to 130 to 135 KHz band or 13.56 MHz band, so that a frequency is relatively low, and therefore the frequency band used in the emission marker 8 can be used in a condition of being hardly influenced by moisture inside and outside the lumen. The frequency band used in the emission marker 8 is set to 130 to 135 KHz band or 13.56 MHz band, so that the emission marker 8 can be used without radio interference with existing systems of 2.45 MHz band used in a wireless LAN or the like, existing systems of 860 MHz to 960 MHz band used in a portable telephone or the like, and the like.

As illustrated in FIG. 6*d*, in another embodiment, the emission marker 8 has an IC chip composed of a control circuit 86 and a memory 87. In the memory 87, identification information can be recorded. The identification information is not limited, and examples of the identification information include names of patients, sexes, privacy information of the patients such as ages, past medical histories and/or current medical states (past histories) of the patient, patient reference numbers, names of operators, names of hospitals, dates of surgery, organ names, information of indwelled positions, and the like. In a case where the emission marker 8 has an IC chip, a reader/writer is provided in the detector 6, so that information of the memory 87 can be read/written. The memory 87 can write data at any time, and therefore can also record how an excised tissue sample having the emission marker 8 having the IC chip indwelled therein is preserved, how the tissue sample is treated, and the like, and can secure traceability. A configuration and an operation method of the IC chip provided in the emission marker 8 are similar to the description of the IC tag marker 1. The control circuit 86 performs control so as to read out the information recorded in the memory 87, and send the information as a signal to the reader of the detector 6 through the coil 82.

EXAMPLE

Production of IC Tag Marker and Detector

An IC tag marker having a maximum diameter of a surface orthogonal to the longitudinal direction of 2 mm was produced. In this IC tag marker, a perforation part is provided at a site where a body is perforated. This IC tag marker is delivered to a digestive tract through a forceps channel (diameter: 3 mm) of a digestive tract endoscope, and indwelled in the vicinity of a tumor through a marking clip available on a market.

A detector having a detection unit, and a support part extending from the detection unit was produced. This detector has a maximum diameter of a surface orthogonal to the longitudinal direction of 10 mm, and can be inserted into an abdominal cavity from a 12 mm port. A body and a support part of the detector are formed of silicone or oxygen free copper (so-called native copper) covered with an insulating film, and therefore correspond to high-temperature and high-pressure steam sterilizing.

An IC tag marker incorporated with an IC chip in the vicinity of a tumor is indwelled by use of a gastrointestinal endoscope before laparoscopic surgery. The IC tag marker is incorporated with a coil type antenna therein, and an antenna of a detector is brought close from the inside of an abdominal cavity, so that a current is generated in the coil type antenna by electromagnetic induction to be supplied to the IC chip. Information recorded in the IC chip is sent to the detector through the coil type antenna, and a reader analyzes the information. In response to the analysis result, a notification unit outputs sound. A detection distance between the IC tag marker and the detector with a piece of meat and water interposed therebetween is allowable up to 3 cm, and the thickness of an intestinal tract wall of a large intestine is about 10 mm, and therefore the IC tag marker can be sufficiently detected by use of the detector.

In Vivo Evaluation Test by Use of Pig Model

A marking clip into which the above IC tag marker was inserted was indwelled in a stomach or a large intestine of a pig model having weight of 30 kg by use of an endoscope camera. More specifically, the perforation part of the IC tag marker was inserted around one of claw parts of an opening/closing arm of a marking clip (long clip, HX-610-135L, manufactured by OLYMPUS CORPORATION). The marking clip into which the IC tag marker was inserted was mounted on a protective sheath tip of a treatment tool for an endoscope. The marking clip through which the IC tag marker was inserted was inserted through a forceps hole of the endoscope from the tip part of the protective sheath and was indwelled in mucosa inside the stomach or the large intestine of the pig model. After the indwelling, the endoscope was removed from the pig model.

A part of an abdomen of the pig model was incised to be mounted with a 12 mm port. The detector was inserted into the abdominal cavity of the pig model through the 12 mm port, and the indwelled IC tag marker was searched. The antenna of the detector was brought close to the IC tag marker, so that sound was generated from the detector. A detection distance between the IC tag marker and the detector with a piece of meat and water interposed therebetween is allowable up to 3 cm, and the indwelling site was able to be accurately identified.

Detection Evaluation Test of IC Tag Marker Using Human Tissue

After approved by the ethics committee of Osaka Medical Center for Cancer and Cardiovascular Diseases, excised specimens of a human were used, and the detection sensitivity of the IC tag marker and the detector was evaluated. The IC tag marker was indwelled in a mucosa surface of the excised digestive tract tissue (stomach tissue or large intestine tissue, respective three examples), and the detector was brought close from a serosal surface. The detector was brought close to the IC tag marker, so that an electromagnetic wave was sensed from the antenna, and sound was generated. All the three examples including the stomach tissue and the large intestine tissue were correctly detected, and the detection error was 10 mm or less.

Production of Emission Marker and Detector

A cylindrical emission marker which has a longitudinal size of 12 mm and a size (diameter) of a surface orthogonal to the longitudinal direction of 3 mm, and is covered and sealed by a polymer base agent of silicone was produced. As the color of an LED, a red color which easily penetrates a lumen wall of an organ was used. This emission marker is delivered to a digestive tract through a forceps channel (diameter: 3 mm) of a digestive tract endoscope, and indwelled in the vicinity of a tumor through a marking clip available on a market.

Additionally, a rectangular parallelepiped detector having a detection unit was produced. This detector has a maximum diameter of a surface orthogonal to the longitudinal direction of 10 mm, and can be inserted into an abdominal cavity from a 12 mm port. A body and a support part of the detector are formed of silicone or oxygen free copper (so-called native copper) covered with an insulating film, and therefore correspond to high-temperature and high-pressure steam sterilizing.

The emission marker is indwelled in the vicinity of a tumor by use of a gastrointestinal endoscope before laparoscopic surgery. An antenna of the detector is brought close from the lumen outside in laparoscopic surgery, so that a current is generated in a coil by electromagnetic induction to be supplied to the LED. As the detector approaches, a generating current increases. With this, light emitted from the LED is strengthened. Additionally, as the detector gets away, the generating current decreases. With this, light emitted from the LED is weakened.

Detection Evaluation Test of Emission Marker Using Human Tissue

Figure 10:
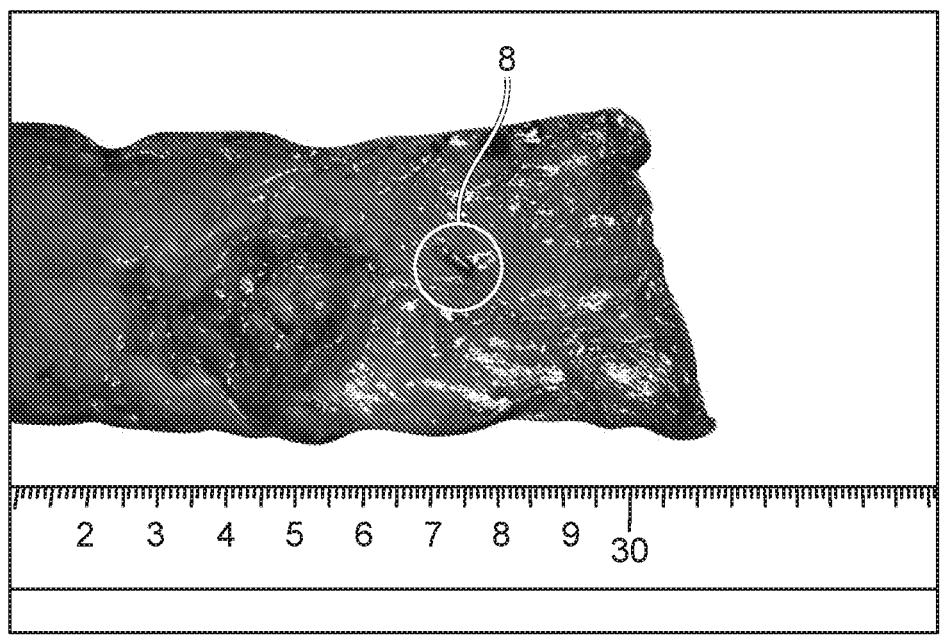
FIG. 10 is a photograph illustrating a result of a detection evaluation test of an emission marker using a human tissue.
Figure 10:
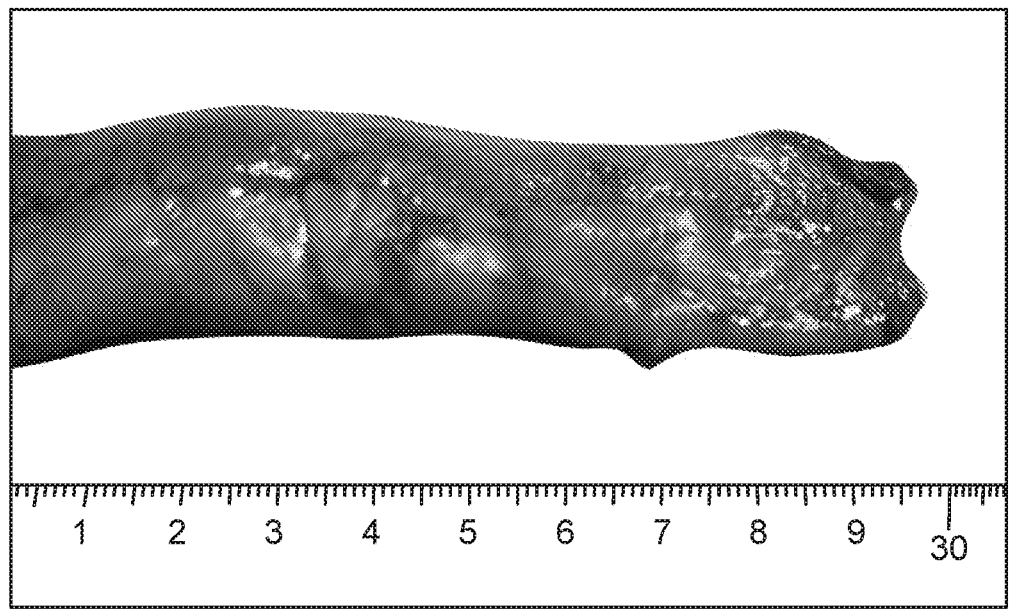
Figure 10:
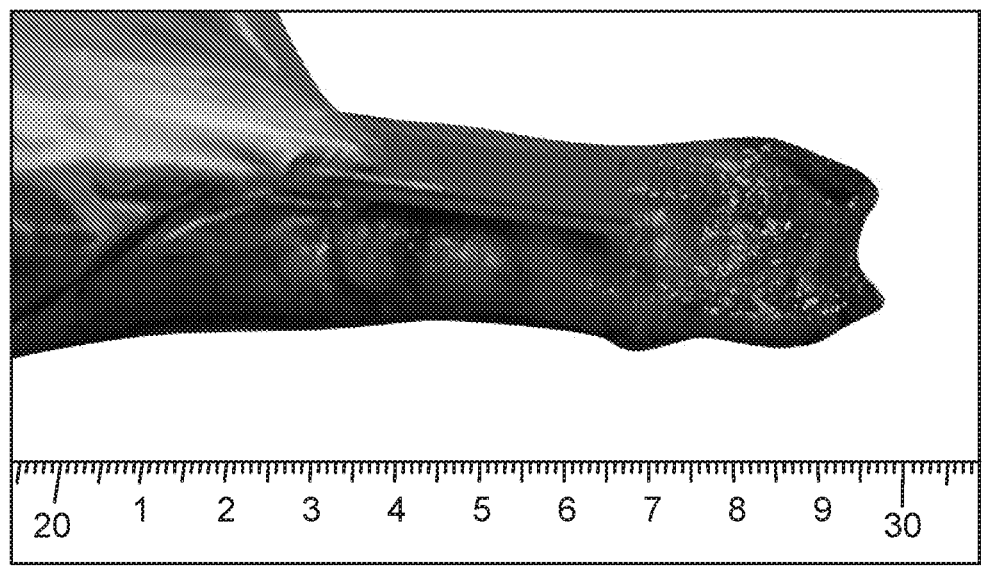
Figure 10:
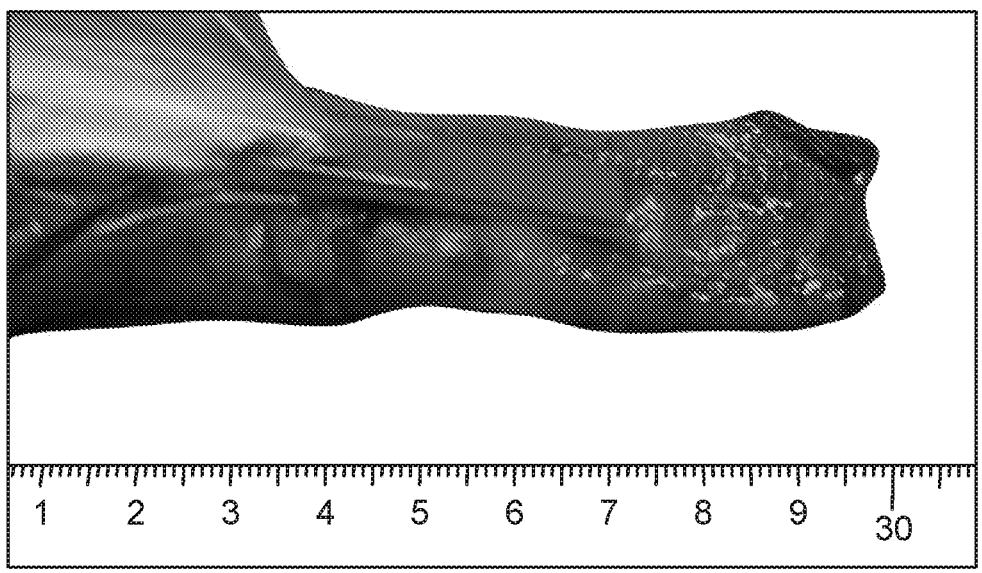

After approved by the ethics committee of Osaka Medical Center for Cancer and Cardiovascular Diseases, excised specimens of a human were used, and the detection sensitivity of the emission marker and the detector was evaluated. The emission marker was indwelled in a mucosa surface of the excised digestive tract tissue (stomach tissue or large intestine tissue, respective three examples) (FIG. 10a). The indwelled emission marker was provided so as to be enwrapped by the mucosa surface of the digestive tract tissue (FIG. 10b). FIG. 10a illustrates the lumen inside, and FIG. 10b illustrates the lumen outside. The detector was gradually brought close to the emission marker from above the lumen. As the detector approaches the emission marker, a current generating in the coil increases. With this, light emitted from the LED is strengthened (FIG. 10c to FIG. 10d). Additionally, it was visually recognized that light was weakly emitted (pale red) in FIG. 10c in which a distance from the detector to the emission marker was long, and light was strongly emitted (deep red) in FIG. 10d in which a distance from the detector to the emission marker was short.

All three examples including the stomach tissue and the large intestine tissue were correctly detected, and the detection error was 5 mm or less.

What is claimed is:

1. A detection system comprising an emission marker and a detector, wherein the emission marker is indwelled in an inner surface of a lumen of a digestive tract which is selected from an esophagus, a stomach, a duodenum, a small intestine, a large intestine, a colon, or a rectum;

the emission marker comprising:
   a base part;
   a coil wound around the base part, wherein the coil receives an induced current from the detector outside the lumen of the digestive tract that is separate from the emission marker;
   an emission part electrically connected to the coil; and
   a cover part for covering at least the base part and the coil,
   wherein the emission part has a light source that emits visible light, and
   wherein the emission marker has a size enabling insertion into a forceps channel of an endoscope, and
   wherein the detector comprises a detection unit having an antenna that acts with the coil of the emission marker.

2. The detection system according to claim 1, wherein the light source of the emission marker is an LED.

3. The detection system according to claim 1, wherein the base part of the emission marker further has a perforation part.

4. The detection system according to claim 1, wherein the cover part of the emission marker is a polymer base agent.

5. A detector for detecting, from outside of a lumen, an emission marker of claim 1 indwelled in the lumen, the detector comprising a detection unit having an antenna that acts with a coil of the emission marker.

6. The detector according to claim 5, wherein the detector is capable of being inserted into a laparoscope port.

7. The detector according to claim 5, wherein at least the detection unit is formed to be high-temperature and high-pressure steam sterilizable.

8. The detection system according to claim 1, wherein the base part of the emission marker further has a memory.

9. An emission marker for being indwelled in an inner surface of a lumen of a digestive tract which is selected from an esophagus, a stomach, a duodenum, a small intestine, a large intestine, a colon, or a rectum, comprising:
   a base part;
   a coil wound around the base part, wherein the coil receives an induced current from outside the lumen of the digestive tract;
   an emission part electrically connected to the coil; and
   a cover part for covering at least the base part and the coil,
   wherein the emission part has a light source that emits visible light, and
   wherein the emission marker has a size enabling insertion into a forceps channel of an endoscope.

* * * * *